(12) United States Patent
Yoon et al.

(10) Patent No.: US 8,951,757 B2
(45) Date of Patent: Feb. 10, 2015

(54) METHOD FOR SELECTIVE LABELING OF PROTEIN PRODUCED BY IN VITRO TRANSLATION BY USING A MARKER FROM TRNA PREPARED BY USING IN VITRO TRANSCRIPTION

(75) Inventors: Seongjun Yoon, Seoul (KR); SooYoun Jun, Seoul (KR); SangHyeon Kang, Seoul (KR)

(73) Assignee: Intron Biotechnology, Inc. (KR)

( * ) Notice: Subject to any disclaimer, the term of this patent is extended or adjusted under 35 U.S.C. 154(b) by 437 days.

(21) Appl. No.: 12/812,382

(22) PCT Filed: Jan. 7, 2009

(86) PCT No.: PCT/KR2009/000057
§ 371 (c)(1),
(2), (4) Date: Jul. 9, 2010

(87) PCT Pub. No.: WO2009/088209
PCT Pub. Date: Jul. 16, 2009

(65) Prior Publication Data
US 2011/0014714 A1    Jan. 20, 2011

(30) Foreign Application Priority Data
Jan. 10, 2008   (KR) ........................ 10-2008-0003081

(51) Int. Cl.
*G01N 33/68*     (2006.01)
*G01N 33/533*    (2006.01)
*G01N 33/532*    (2006.01)
*C12P 19/34*     (2006.01)
*C07H 21/02*     (2006.01)

(52) U.S. Cl.
CPC ............ *G01N 33/533* (2013.01); *G01N 33/532* (2013.01)
USPC ........................................ 435/91.3; 536/23.1

(58) Field of Classification Search
CPC ........................... G01N 33/582; G01N 33/583
USPC ........................................ 435/91.3; 536/23.1
See application file for complete search history.

(56) References Cited

U.S. PATENT DOCUMENTS
7,385,038 B2   6/2008   Hohsaka et al.

FOREIGN PATENT DOCUMENTS
KR   1020050076334   7/2005
WO   WO 96/14426 A1   5/1996

OTHER PUBLICATIONS

Gite et al.; Ultrasensitive Fluorescence-Based Detection of Nascent Proteins in Gels; Analytical Chemistry; vol. 279; pp. 218-225; (2000).*
Hohsaka et al.; Efficient Incorporation of Nonnatural Amino Acids with Large Aromatic Groups into Streptavidin in in Vitro Protein Synthesizing Systems; Journal of the American Chemical Society; vol. 121; pp. 34-40; published online Dec. 19, 1998.*
Hohsaka Supporting Information; Supporting Information for the article Efficient Incorporation of Nonnatural Amino Acids with Large Aromatic Groups into Streptavidin in in Vitro Protein Synthesizing Systems; Journal of the American Chemical Society; vol. 121; pp. 1-13; published 1998.*
Invitrogen; T7 RNA polymerase technical bulletin 8033-1; pp. 1-7; (2002).*
Korencic et al.; A one-step method for in vitro production of tRNA transcripts; Nucleic Acid Research; vol. 30, No. 20, e105, pp. 1-4 (2002).*
Johnson et al., Nepsilon-acetyllysine transfer ribonucleic acid: a biologically active analogue of aminoacyl transfer ribonucleic acids, Biochemistry. Feb. 10, 1976;15(3):569-75.
Noren et al., A general method for site-specific incorporation of unnatural amino acids into proteins, Science. Apr. 14, 1989;244(4901):182-8.
Kim et al., A highly efficient cell-free protein synthesis system from *Escherichia coli*, Eur J Biochem. Aug. 1, 1996;239 (3):881-6.
Kigawa et al., Cell-free production and stable-isotope labeling of milligram quantities of proteins, FEBS Lett. Jan. 8, 1999;442(1):15-9.
Hohsaka et al., Incorporation of non-natural amino acids into proteins, Curr Opin Chem Biol. Dec. 2002;6(6):809-15.
Jun et al., Fluorescent labeling of cell-free synthesized proteins with fluorophore-conjugated methionylated tRNA derived from in vitro transcribed tRNA.,J Microbiol Methods. Jun. 2008;73(3):247-51.
Kang et al., Fluorescent labeling of cell-free synthesized proteins by incorporation of fluorophore-conjugated nonnatural amino acids, Anal Biochem. Jan. 1, 2007;360(1):1-6.
Mamaev et al., Cell-free N-terminal protein labeling using initiator suppressor tRNA,Anal Biochem. Mar. 1, 2004;326 (1):25-32.
International Search Report in International Application No. PCT/KR2009/000057 dated Aug. 27, 2009.
Written Opinion in International Application No. PCT/KR2009/000057 dated Aug. 27, 2009.

* cited by examiner

*Primary Examiner* — Jim Ketter
*Assistant Examiner* — Antonio Galisteo Gonzalez
(74) *Attorney, Agent, or Firm* — Meunier Carlin & Curfman, LLC

(57) ABSTRACT

The present invention relates to a method for the preparation of a labeling agent derived from one type of tRNA prepared by in vitro transcription, which is usable for non-radioactive selective labeling of target proteins produced by in vitro translation with fluorophore or biotin; and a method for selective labeling of target proteins produced by in vitro translation using the labeling agent without labeling pre-existing proteins in the reaction mixture.

3 Claims, 3 Drawing Sheets

SEQUENCE LISTING

```
<160> NUMBER OF SEQ ID NOS: 3

<210> SEQ ID NO 1
<211> LENGTH: 120
<212> TYPE: DNA
<213> ORGANISM: Artificial Sequence
<220> FEATURE:
<223> OTHER INFORMATION: Synthetic construct: sense oligonucleotide

<400> SEQUENCE: 1
aattctaata cgactcacta tacgcggggt ggagcagcct ggtagctcgt cgggctcata      60
acccgaaggt cgtcggttca aatccggccc ccgcaaccac aggatccgca tccttctgca     120

<210> SEQ ID NO 2
<211> LENGTH: 112
<212> TYPE: DNA
<213> ORGANISM: Artificial Sequence
<220> FEATURE:
<223> OTHER INFORMATION: Synthetic construct: antisense oligonucleotide

<400> SEQUENCE: 2
gaaggatgcg gatcctgtgg ttgcgggggc cggatttgaa ccgacgacct tcgggttatg      60
agcccgacga gctaccaggc tgctccaccc cgcgtatagt gagtcgtatt ag             112

<210> SEQ ID NO 3
<211> LENGTH: 77
```

```
<212> TYPE: DNA
<213> ORGANISM: Artificial Sequence
<220> FEATURE:
<223> OTHER INFORMATION: Synthetic construct: initiation methionine tRNA

<400> SEQUENCE: 3
cgcggggtgg agcagcctgg tagctcgtcg ggctcataac ccgaaggtcg tcggttcaaa      60
tccggccccc gcaacca                                                    77
```

METHOD FOR SELECTIVE LABELING OF PROTEIN PRODUCED BY IN VITRO TRANSLATION BY USING A MARKER FROM TRNA PREPARED BY USING IN VITRO TRANSCRIPTION

TECHNICAL FIELD

The present invention relates to a preparation method of the selective labeling material (agent) of proteins produced by in vitro translation (cell-free protein synthesis), and a method for selective labeling of protein using the same. More precisely, the present invention relates to a method for the preparation of a non-radioactive labeling material (labeling agent) in order to avoid the risk accompanied by use of the conventional radioisotope in labeling of cell-free synthesized proteins, using one kind of tRNA produced by in vitro transcription instead of total tRNA mixture as a tRNA material; and a method for selective labeling of cell-free synthesized proteins using the said selective labeling material.

BACKGROUND ART

In vitro translation is the method producing protein quickly in a reactor without performing cell culture. In the early days of in vitro translation, lower protein productivity was a serious problem. However, it has turned into a very efficient protein production method owing to the optimization of reaction condition and the advanced design of the reactor resulted from the continuous studies by many research groups (Eur. J. Biochem. 239: 881-886, 1996; FEBS Lett. 442: 15-19, 1999).

To increase availability of in vitro translation, it is also required to develop a more efficient and convenient detection method of the cell-free synthesized proteins in addition to the method of improving protein productivity itself. To detect the cell-free synthesized protein easily, a method for selective labeling of the target protein produced from DNA template via translation is required. The selective labeling is very important for the detection because there are already numbers of proteins in the cell-free protein synthesis reaction mixture including enzymes necessary for the production of the target protein. The most widely used method for selective labeling the cell-free synthesized protein is the labeling with radioisotope. In this method, an amino acid labeled with radioisotope is added to the cell-free protein synthesis reaction mixture and then the amino acid is inserted into the growing polypeptide, suggesting that the produced protein is labeled with the radioisotope. At this time, pre-existing proteins in the mixture are not labeled with the radioisotope because those are not the ones that are newly produced, indicating that there is no insertion of the radioisotope into the existing proteins. This conventional method using radioisotope is convenient for labeling the newly produced protein but has a risk of exposing the experimenter on radioactivity. Another disadvantage of this method is inconvenience in the restricted dealing with radioactive materials and radioactive waste.

So, a novel non-radioactive labeling method using fluorophore (fluorescent dye) or biotin, instead of radioisotope, has been developed in order to label and detect the produced protein easily and at the same time in order to solve the problems and inconvenience of the conventional method using radioisotope. The most common non-radioactive labeling method for the selective labeling of cell-free synthesized protein is the method developed by Johnson et al (Biochemistry 15:569-575, 1976). In the method developed by Johnson et al, one amino acid is selected for the labeling of cell-free synthesized protein. Then, an appropriate tRNA corresponding to the selected amino acid is conjugated to the selected amino acid by using aminoacyl-tRNA synthetases. This conjugation reaction between the amino acid and its corresponding tRNA is called aminoacylation. After aminoacylation, fluorophore or biotin for labeling is conjugated to the amino acid constituting the aminoacylated tRNA through functional group on the side chain of the amino acid or α-amino group of initiator methionine constituting the aminoacylated tRNA. As a result, the fluorophore- or biotin-conjugated aminoacylated tRNA was prepared by the above process, which is summarized in FIG. 1. The fluorophore- or biotin-conjugated aminoacylated tRNA used for selective labeling of cell-free synthesized proteins is called "tRNA conjugate for labeling" here in this invention.

The aminoacyl-tRNA synthetases used for aminoacylation have high substrate specificity (these enzymes accept 20 different natural amino acids as a substrate and do not accept non-natural amino acids except only a few). Because of such substrate specificity, the fluorophore- or biotin-conjugated amino acid cannot be conjugated to tRNA by aminoacylation mediated with aminoacyl-tRNA synthetases. Therefore, it is necessary to prepare the aminoacylated tRNA first and later on try to conjugate fluorophore or biotin thereto.

To label the cell-free synthesized protein using "tRNA conjugate for labeling", the "tRNA conjugate for labeling" is simply added to the in vitro translation reaction mixture. Then, when a protein is generated from DNA, the fluorophore- or biotin-conjugated amino acid is inserted into a growing polypeptide, resulting in the labeling of the cell-free synthesized protein with the fluorophore or biotin.

According to the conventional method developed by E. Johnson, et al, "total tRNA mixture" was used as a tRNA material in the process of preparing the "tRNA conjugate for labeling" for the selective labeling of cell-free synthesized protein. The "total tRNA mixture" indicates the mixture of different types of tRNAs. When the tRNA mixture was used as a tRNA material, following problems were notified. First, when the "total tRNA mixture" was used as a tRNA material, there was a question of efficiency. Despite all different tRNAs provided, it was only one type of tRNA that was actually used for the preparation of "tRNA conjugate for labeling". That is, only the one that corresponded to the designated amino acid selected by the person who tried to produce the "tRNA conjugate for labeling" was used alone, and no other tRNAs were used at all. That is, there were way many tRNAs remaining unused rather being used. Those unused tRNAs followed the tracks of production of the "tRNA conjugate for labeling" all the time and at last they were included in the final "tRNA conjugate for labeling". Those tRNAs not corresponding to the selected amino acid could not be conjugated to the selected amino acid, so that they could not be conjugated afterwards to the fluorophore or biotin, either, which means they were useless for the preparation of "tRNA conjugate for labeling".

When the "tRNA conjugate for labeling" that contains unnecessary impurities, unpaired remaining tRNAs, is used for the labeling of cell-free synthesized protein, the efficiency of protein labeling is accordingly decreased. Besides, signals of those final labeled proteins are not so good, either. That is, signal-to-noise ratio is decreased. This is because fluorophore or biotin is non-specifically bound to the backbone of the unpaired tRNA with generating background fluorescence at the final analysis of labeled protein.

tRNA directly conjugated with fluorophore or biotin through its backbone decreases solubility of the "tRNA conjugate for labeling", the active ingredient for the protein labeling, indicating that it is difficult to prepare the high concentration of the final "tRNA conjugate for labeling". To obtain enough signals of labeled protein, a huge amount of "tRNA conjugate for labeling" has to be added. If that is the case, the co-added amount of unnecessary tRNAs is also increased, resulting in more serious background fluorescence.

Considering the above problem, when the conventional method was performed, chromatographic purification was used for the isolation of pure "tRNA conjugate for labeling" after the production of "tRNA conjugate for labeling". But, this purification of pure "tRNA conjugate for labeling" is very complicated and takes much time.

The present inventors had a belief that the development of a novel preparation method of "tRNA conjugate for labeling" that does not require any additional purification and isolation process was quite necessary and useful in the end. The present inventors were sure that this novel method could be achieved by using only one type of tRNA corresponding to the selected amino acid, instead of "total tRNA mixture", for the production of "tRNA conjugate for labeling".

To use only one type of tRNA as a tRNA material for the production of "tRNA conjugate for labeling", it is theoretically possible to separate only one type of tRNA from total tRNA mixture before aminoacylation. But in reality, it is very difficult to separate one type of tRNA from tRNA mixture because tRNAs are similar to one another in their physical characteristics. So, this could be more difficult and less efficient than the purification and separation of a necessary "tRNA conjugate for labeling" from the final "tRNA conjugate for labeling" preparation.

A more reasonable approach has been made as follows: A gene containing genetic information of a specific tRNA is inserted in cells, and the cells having the gene corresponding to specific tRNA are cultured, resulting in the over-expression of tRNA therein. Then, the cells are harvested and disrupted. Finally, the tRNA is separated from the obtained cell lysate (Proc. Natl. Acad. Sci, USA 84: 334-338, 1987). However, this method also has a problem of contamination of tRNA preparation with unwanted endogenous tRNAs. That is, many types of endogenous tRNAs always exist in the cells at a certain level, indicating the risk of contamination of impurities (different types of endogenous tRNAs) is still there. Even though the ratio of a target tRNA is comparatively higher than that of the case using total tRNA mixture prepared from normal cells, the margin is not so significant and the additional purification is still needed.

DISCLOSURE

Technical Problem

It is an object of the present invention to solve the technical problem of the conventional art and accordingly to achieve the requested novel method.

The present inventors eliminated the necessary step of purification and separation of "tRNA conjugate for labeling" which was inevitable process in the conventional art by using only one type of tRNA prepared by in vitro transcription instead of using "total tRNA mixture" as a tRNA material for the production of "tRNA conjugate for labeling". In addition, the present inventors succeeded in obtaining a labeled protein providing improved signals even with using the "tRNA conjugate for labeling" as it was without complicated chromatographic purification, compared with that produced by using "tRNA conjugate for labeling" prepared by the conventional art.

Therefore specifically, it is an object of the present invention to provide a novel preparation method of "tRNA conjugate for labeling" providing much improved signals in protein labeling with ease. It is another object of the present invention to provide a method for selective labeling of a cell-free synthesized protein using the "tRNA conjugate for labeling" prepared by the method of the invention.

Technical Solution

To achieve the above objects, the present invention provides a novel preparation method of "tRNA conjugate for labeling" that can provide more improved signals than the "tRNA conjugate for labeling" prepared by the conventional method and does not require the chromatographic purification process which was required in the conventional art using "total tRNA mixture" as a tRNA material in the production of "tRNA conjugate for labeling", in order to non-radioactively label a cell-free synthesized protein.

The present inventors designed a novel preparation method of "tRNA conjugate for labeling", in which only one type of tRNA (called "a specific tRNA" in this description) that corresponds to codon on the DNA of the selected amino acid (designated for protein labeling) is used as a tRNA material for the production of "tRNA conjugate for labeling", leading to the completion of this invention. The present invention thus provides a method for preparation of "tRNA conjugate for labeling" providing improved signals, compared with the conventional "tRNA conjugate for labeling" prepared by the conventional art, which does not require an additional chromatographic purification procedure and makes the preparation easy and quick.

The present invention provides a preparation method of "tRNA conjugate for labeling" useful for the selective labeling of proteins produced by in vitro translation, which comprises the following steps:

1) preparing one type of tRNA (specific tRNA) corresponding to the codon on DNA of the amino acid selected for protein labeling by in vitro transcription;

2) performing conjugation of the tRNA prepared in step 1) and the specific amino acid corresponding to the tRNA by aminoacylation; and 3) preparing "tRNA conjugate for labeling" by conjugating fluorophore or biotin to functional group existing on the side chain of amino acid or α-amino group of initiator methionine constituting the aminoacylated tRNA prepared in step 2).

The present invention also provides a method for labeling and detection of the protein produced by in vitro translation by using the "tRNA conjugate for labeling" prepared by the above method.

The present invention further provides a reagent for the detection of cell-free synthesized protein comprising the "tRNA conjugate for labeling" prepared by the above method.

Genetic information of the amino acid sequence of protein is included in DNA codon. DNA codon consists of three base pairs. More specifically, it is composed of combinations of nucleotide having one of four bases, A (adenine), T (thymine), G (guanine), and C (cytosine). For example, GGG is the codon corresponding to glycine, GCC is the codon corresponding to alanine, and ATG is the codon corresponding to methionine. In this codon, there is a specific tRNA corresponding to the codon. There are 61 DNA codons corresponding to natural amino acids except three stop codons and accordingly there are matching numbers of tRNA corresponding to those DNA codons. Strictly, tRNA corresponds to mRNA transcribed from DNA, but it is understood by those in the art that the strict definition of tRNA cannot limit the present invention.

In vitro transcription facilitates high purity and high efficiency production of a specific tRNA. In the method called nonsense suppression, a non-natural amino acid is inserted in a protein by using suppressor-tRNA prepared by in vitro transcription, which is completely different from the method of Johnson, et al even though it seems like similar (Chem. Biol. 3: 685-691, 1997; Nucleic Acids Res. 18: 83-88, 1990). According to the method designed by Johnson, et al which is the preparation method of "tRNA conjugate for labeling" useful for the labeling of cell-free synthesized protein, it is unusual to use tRNA prepared by in vitro transcription as a tRNA material for the production of "tRNA conjugate for labeling". Even though many non-natural amino acids containing a fluorophore-labeled non-natural amino acid were successfully inserted in a protein by nonsense suppression (Science 244: 182-188, 1989; Curr. Opin. Chem. Biol. 6: 809-815, 2002), it was judged to be inappropriate method for general labeling of cell-free synthesized protein, because this method required the step of pre-insertion of nonsense codon in DNA or mRNA template having genetic information of the target protein for expression and this method required a suppressor tRNA complementary thereto. That is, this nonsense suppression is the method that can be performed by using a specific material in a specific occasion.

It is the only duty of an experimenter to add the "tRNA conjugate for labeling" prepared by the above method to the cell-free protein synthesis reaction mixture, in order to label the cell-free synthesized protein selectively. That is, once the "tRNA conjugate for labeling" is added to the cell-free protein synthesis reaction mixture, a fluorophore- or biotin-labeled amino acid is inserted in the protein generated from the mixture, suggesting that the cell-free synthesized protein is necessarily labeled by fluorophore or biotin. The cell-free protein synthesis reaction mixture containing the labeled protein can proceed to electrophoresis according to the conventional procedure. Then, the gel obtained from electrophoresis can be analyzed to detect the labeled protein. In this gel analysis, if the cell-free synthesized protein is labeled with fluorophore, this labeled protein can be detected by fluorescence image analyzer (equipped with UV irradiating device and image analyzer). If the cell-free synthesized protein is labeled with biotin, it can be detected by avidin-biotin complex method. This detection method is indicated as western blotting in this invention for convenience. This avidin-biotin complex method has been well-known and well-performed by those in the art, which means this method is very general and thus no further explanation is necessary.

The preparation of "tRNA conjugate for labeling" using a specific kind of tRNA prepared by in vitro transcription is described in detail hereinafter. First, a plasmid having genetic information about the specific tRNA to be used as a template for in vitro transcription is constructed. Once enough amount of the plasmid is prepared, they are linearized with a restriction enzyme. After the linearization, in vitro transcription is performed using the enzyme-treated plasmid solution as a template solution to obtain the specific tRNA with high purity and high efficiency. After preparing the specific tRNA by in vitro transcription, this target tRNA is conjugated to a specific amino acid matching the prepared tRNA. When the aminoacylated tRNA is prepared, fluorophore or biotin is finally conjugated to the α-amino group of initiator methionine or the functional group of the side chain of the amino acid constituting the aminoacylated tRNA, resulting in the preparation of "tRNA conjugate for labeling".

In an example of the present invention, methionine was selected as a target amino acid and the α-amino group of methionine was used as a functional group for the conjugation with fluorophore or biotin. Particularly, initiator methionine was used for the conjugation. However, the applicable amino acid of the present invention is not limited in methionine and any of 20 natural amino acids can be used. Because each amino acid has different functional groups, the functional group should be considered in selecting the amino acid. The structure of amino acid is presented in FIG. 2. In FIG. 2, the functional group used for the conjugation with fluorophore or biotin for the production of "tRNA conjugate for labeling" was α-amino group of initiator methionine and the side chain of the amino acids. The α-amino group is only applicable when initiator methionine is used. In general, there are 20 natural amino acids including leucine and glycine, etc. So, the selection of an amino acid among them is the first thing to do for the realization of this invention. Then, one codon applicable and corresponding to the selected amino acid needs to be determined. In general, there are several codons corresponding to one amino acid. For example, histidine has CAT and CAC for its corresponding codons, and proline has CCT, CCC, CCA and CCG for its corresponding codons. After determining which codon will be used, determination of a target tRNA is made. That is, tRNA counterpart is selected depending on its corresponding DNA codon. All the genetic information of tRNA corresponding to each codon is all informed which is easily distinguished. Therefore, further explanation is not necessary herein. Information of tRNA corresponding to each codon is well known to those in the art who can easily identify and recognize them to obtain.

To prepare a target specific tRNA to have the same structure as the natural tRNA by in vitro transcription, it has to be transcribed exactly as designed not to have any additional base in addition to the original bases included in the natural tRNA. To do so, in vitro transcription has to be achieved exactly in the DNA region corresponding to the total base combination of tRNA. The template plasmid for in vitro transcription is supposed to be cut at the boundary between the corresponding area and non-corresponding area to the total base of a specific tRNA in stead of using the circular form of the plasmid as it is. That is, transcription is forced to stop right there. To cut the plasmid at the next base to the corresponding area to the total base of tRNA, restriction enzyme recognition sequence to be used for the linearization of the plasmid has to be pre-inserted. In an example of the present invention, Fok I was used as the restriction enzyme for the linearization of the plasmid, but other enzymes can also be used in this invention as long as the selected restriction enzyme is capable of making the plasmid blunt end. That is, a restriction enzyme that can cut the plasmid without forming overhang is preferred. Such preferable enzymes are exemplified by Sma I, Hinc II, EcoR V, EcoICR I, and Alu I, etc. If any other enzyme is selected, the restriction enzyme recognition sequence suitable for the enzyme has to be inserted into the plasmid. If this selection is inconvenient, it is preferred to select Fok I as in the example of the present invention.

In a preferred embodiment of the present invention, as fluorophore to be conjugated to an amino acid, three kinds of fluorescent materials including 5-carboxyfluorescein (5-FAM) are proposed, but not limited thereto and other fluorescent materials such as Dansyl, Fluorescein, Texas Red, Cascade Blue, Cascade Yellow, Erythrosin, Coumarin, NBD, Pacific Blue, PyMPO, Pyrene, Phycoerythrin, Cy2, Cy3, Cy5, Cy7, and NBD-Phallacidin (all brand names) can also be used.

A variety of chemical reactions can be utilized to conjugate fluorophore or biotin to the amino acid constituting the aminoacylated tRNA, which are exemplified by condensation, acylation, esterification, and reductive alkylation, etc. In this invention, condensation was utilized, but not limited thereto.

To select a proper chemical reaction, the functional group of the selected amino acid is one factor to be considered. This process is well known and easily done by those in the art, so the detailed explanation is not given herein.

To attach fluorophore or biotin to the amino acid constituting the aminoacylated tRNA by a certain chemical reaction, the selected fluorophore or biotin has to be derivatized as an appropriate derivative form for the selected reaction. In general, fluorophore or biotin itself does not have enough reactivity for any chemical reaction. Therefore, it is necessary to prepare them in an appropriate derivative form. The derivative form can be succinimidyl ester, isothiocyanate, carboxylic acid, and sulfonyl chloride, etc. These derivatives can be directly prepared by organic synthesis by experimenters, or commercial derivatives can be purchased if an experimenter is not familiar with such organic synthesis or if he or she simply wants an easier way. There are many derivative forms commercialized already in the market. In this invention, succinimidyl ester of fluorophore or biotin was used, but not always limited thereto.

The protein that can be labeled by the method of the present invention is not limited and any protein that can be produced by in vitro translation can be used without limitation. No matter a protein has been fully discovered in its biological functions or not, the protein can be a target of this invention.

Advantageous Effect

According to the present invention, the "tRNA conjugate for labeling" used for non-radioactive labeling of the cell-free synthesized protein can be easily prepared without a complicated chromatographic purification process. That is, tRNA prepared by in vitro transcription can be used as a tRNA material instead of "total tRNA mixture", suggesting that "tRNA conjugate for labeling" can be prepared with high purity without purification processes more easily than any other conventional way. When a protein produced by in vitro translation is labeled by using the "tRNA conjugate for labeling" produced by the method of the invention, much improved protein signals can be provided in the final protein detection. That is, compared with the conventional method, background is significantly reduced, resulting in the improved signals. Besides, the method of the present invention is safer and easier and facilitates the detection of a target protein produced from various genes rapidly and further facilitates the detection of proteins expressed from a huge amount of genes in a short period of time, so that it can be effectively used for high throughput gene screening. The method of the present invention can also be used in the field of drug discovery or development of a novel drug, for example in preparation of target proteins and detection thereof and analysis of functions of various genes, etc.

So, the present invention can be utilized for the study of proteomics recently attracting our attention in relation to the studies of gene expression, protein identification, protein functions and structures, etc. The present invention is also useful for the detection of protein production performed in basic experiments for the medicinal, industrial and academic experiments. Further, the present invention can be effectively used for the detection of a target protein expression necessary for the disclosure of functions of newly identified genes.

DESCRIPTION OF DRAWINGS

The application of the preferred embodiments of the present invention is best understood with reference to the accompanying drawings, wherein:

As shown in FIG. 1, in the structure of the "tRNA conjugate for labeling", tRNA-amino acid-fluorophore is arranged in that order or tRNA-amino acid-biotin is arranged in that order.

Figure 1:
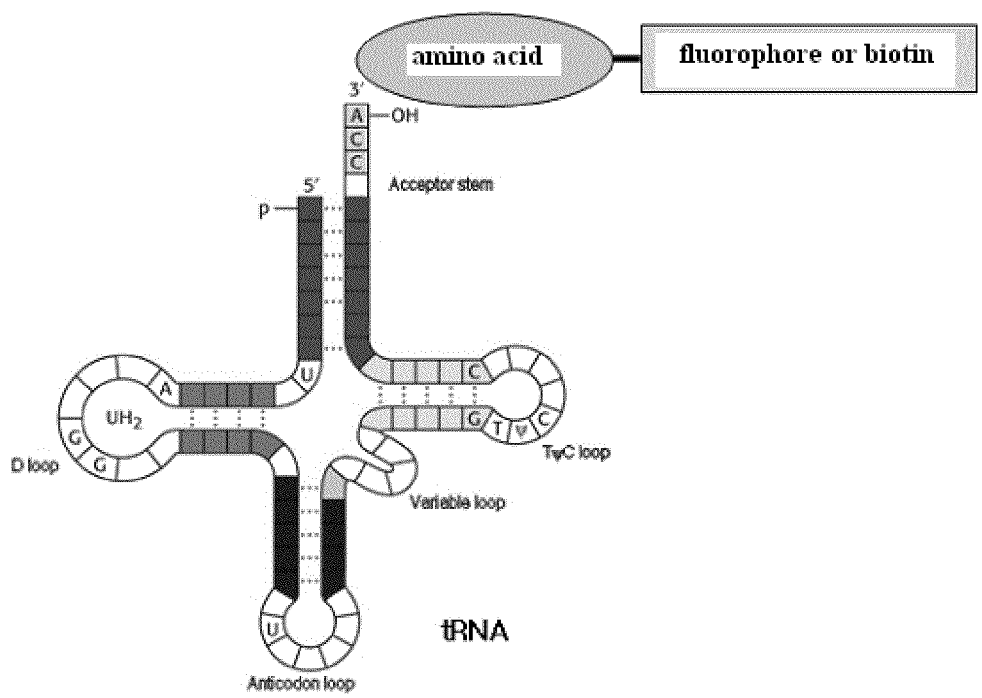
FIG. 1 is a schematic diagram illustrating the general structure of "tRNA conjugate for labeling".
Figure 2:
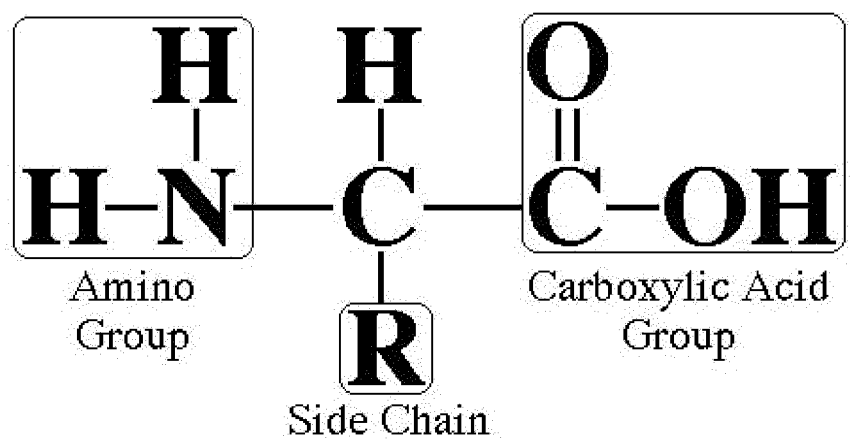
FIG. 2 is a diagram illustrating the structure of amino acid.

Lane 2 shows the reaction performed with the biotin-conjugated "tRNA conjugate for labeling" prepared by using the specific tRNA produced by in vitro transcription in the presence of EPO gene.

BEST MODE

Practical and presently preferred embodiments of the present invention are illustrative as shown in the following Examples.

However, it will be appreciated that those skilled in the art, on consideration of this disclosure, may make modifications and improvements within the spirit and scope of the present invention.

In a preferred embodiment of the present invention, the preparation of a plasmid containing the genetic information about a specific tRNA to be used as a template for in-vitro transcription is illustrated in example 1. Linearization of the plasmid prepared in example 1 using a restriction enzyme capable of making the plasmid blunt end is illustrated in example 2. In vitro transcription with the linearized plasmid solution prepared in example 2 is illustrated in example 3. The preparation of cellular extract containing intracellular components necessary for cell-free protein synthesis is illustrated in example 4. The separation of an enzyme (that is, aminoacyl-tRNA synthetase), which is used to conjugate the amino acid to the tRNA prepared in example 3, from the cellular extract prepared in example 4 is illustrated in example 5. The conjugation of the amino acid and tRNA prepared in example 3 using the aminoacyl-tRNA synthetase separated in example is illustrated in example 6. The conjugation of fluorophore with the amino acid constituting the aminoacylated tRNA prepared in example 6 is illustrated in example 7. The conjugation of biotin with the amino acid constituting the aminoacylated tRNA prepared in example 6 is illustrated in example 8. Labeling of the protein produced by in vitro translation using the fluorophore-conjugated "tRNA conjugate for labeling" and the detection of the labeled protein are illustrated in example 9. Labeling of the protein produced by in vitro translation using the biotin-conjugated "tRNA conjugate for labeling" and the detection of the labeled protein are illustrated in example 10. In example 9, to investigate the effectiveness of the fluorophore-conjugated "tRNA conjugate for labeling", chloramphenicol acetyltransferase (CAT) was used as a model protein, and erythropoietin (EPO) and dihydrofolate reductase (DHFR) were additionally selected for the investigation of the applicability of the present invention to different proteins. In example 10, EPO was selected to investigate the effectiveness of the biotin-conjugated "tRNA conjugate for labeling".

Hereinafter, cell-free synthesis and non-radioactive labeling of some proteins including CAT are illustrated in detail in the following examples. These selected proteins are only applicable examples and cannot limit the spirit and scope of the present invention. Basically every protein that can be produced by in vitro translation can be used in this invention. The application of the present invention can be made to any protein no matter its characteristics have been disclosed or not. In a preferred embodiment of the present invention, succinimidyl ester derivative was used, but it was still one of many derivatives that can be used in this invention. Thus, the present invention is not limited thereto. In another preferred embodiment of the present invention, methionine was used as a model amino acid, but this was also an example of many other amino acids that can be applied to the present invention. So, the present invention is not limited thereto either.

Example 1

Construction of a Plasmid having the Genetic Information about a Specific tRNA

To construct a plasmid having the genetic information of a specific tRNA, a DNA fragment containing the sequences of the specific tRNA, restriction enzyme recognition sites necessary for cloning into vector and linearization of the plasmid, and the promoter necessary for in vitro transcription was prepared first by oligonucleotide annealing in this example. To prepare such DNA fragment, the total nucleotide sequence of a target DNA fragment had to be designed first, and the following sequences were selected for the design. In this example, initiator methionine was selected as a model amino acid. So, the sequence of tRNA that corresponded to initiator methionine was selected. Next, Fok I was selected as a restriction enzyme for linearization of the plasmid, so the recognition sequence thereof was selected. EcoR I and Pst I recognition sequences were selected because EcoR I and Pst I were used for cloning into the vector. T7 promoter sequence was also selected because T7 promoter was supposed to be used for in vitro transcription. The above mentioned sequences were all included in the total sequence of the DNA fragment. The nucleotide sequence of the finally designed DNA fragment was the nucleotide sequence of the following oligonucleotide.

There is no limitation in selecting a promoter for in vitro transcription and SP6 promoter can also be accepted. Thus, the selection of a promoter depends on an experimenter. The experimenter can also select a tRNA sequence, a restriction enzyme recognition sequence, and a promoter sequence for the design of a DNA fragment, and information on these sequences has already been informed. The sequence design of a DNA fragment using such informed sequences is well known to those in the art, so that details are not given herein.

To generate the designed DNA fragment, two complementary oligonucleotides were prepared. These oligonucleotides can be easily produced by a company specialized in this field.

The sense oligonucleotide sequence was 5'-AATTCTAATACGACTCACTATA CGCGGGGTGGAGCAGCCTGGTAGCTCGTCGGGC TCATAACCCGAAGGTCGTCGGTTCAAATCCGGCCC CCGCAACCA<u>CAGGATCCGCATCCTTCTG</u> CA-3' (SEQ. ID. NO: 1), and the antisense oligonucleotide sequence was 5'-GAAGGATGCGGATCCTG TGGTTGCGGGGGCCGGATTTGAACCGACGACCTTC GGGTTATGAGCCCGACGAGCTACCAGGCTGCTCCA <u>CCCCGCGTATAGTGAGTCGTATTAG</u>-3' (SEQ. ID. NO: 2). The underlined part (SEQ. ID. NO: 3) of those two oligonucleotides corresponded to tRNA sequence matching the initiator methionine selected in this example. If another amino acid is selected, this part will be replaced with another tRNA sequence that corresponds to the amino acid. The synthesized oligonucleotides were dissolved in molecular biological grade water and equal amount of each oligonucleotide was mixed in the polymerase chain reaction (PCR) tube. Annealing of those two oligonucleotides was performed using a thermal cycler with the following profile: (1) heat to 95° C. for 2 minutes, (2) cool to 65° C. for 5 minutes, and (3) proceed to 37° C. for 30 minutes. Upon completion of annealing, the annealed DNA fragment was digested with EcoR I and Pst I to expose the region for cloning and then the restriction enzyme-treated DNA fragment was recovered, followed by cloning into a vector. In the meantime, the vector for cloning, pUC19, was also digested with EcoR I and Pst I, being prepared as a suitable form for cloning of the DNA fragment. The recovered DNA fragment and the recovered pUC19 fragment were ligated using DNA ligase. As a result, the final plasmid was constructed. In this example, pUC19 was used as the vector for the construction of the plasmid, but any other vector, no matter it is constructed by an experimenter or purchased, can be used in this invention without limitation.

To increase transcription efficiency in this example, the first base (C) of the sequence of tRNA corresponding to initiator methionine was mutated to G by site-directed mutagenesis. The previous report said that such mutation increased transcription efficiency (Nat. Biotechnol. 20: 723-728, 2002). This mutation was only for the increase of transcription efficiency, and not always required.

*E. coli* was transformed with the plasmid constructed above and the amplified plasmid in transformants was recovered in a large scale, which was then used for the linearization.

Example 2

Plasmid Linearization by Restriction Enzyme

The plasmid prepared in example 1 was linearized by using a restriction enzyme capable of making the plasmid blunt end before being used as a template in in-vitro transcription. The restriction enzyme used in this example was Fok I. Digestion with Fok I restriction enzyme was performed in 100 µl volumes at 37° C. for 16 hours as follows. The reaction conditions can be adjusted by an experimenter and it is easy and preferred to follow the manufacturer's instructions. 1× restriction enzyme buffer (Intron Biotechnology; 10 mM Tris-HCl (pH7.5), 10 mM $MgCl_2$, 1 mM dithiothreitol (DTT), 50 mM NaCl), 20 µg of plasmid, 50 unit Fok I (Intron Biotechnology), and 0.01% bovine serum albumin (BSA). In this restriction enzyme digestion, it is preferred to digest the plasmid as complete as possible. If the amount of the plasmid added to the restriction enzyme reaction is too much or the amount of the restriction enzyme is too less, the plasmid cannot be cut completely. To cut the plasmid effectively, it is important to regulate the ratio of the plasmid to the restriction enzyme. The present inventors confirmed that it was most preferred that the plasmid was added at the concentration of 0.2 µg/µl and the restriction enzyme was added at the concentration of 0.5 U/µl or more. Generally, a plasmid is completely digested when a restriction enzyme is added at the ratio of 2.5 unit per 1 µg of the plasmid. When BSA was added, the digestion efficiency of the restriction enzyme was rather increased.

Example 3

In vitro Transcription by using Linearized Plasmid

The solution containing the plasmid linearized by Fok I was used as a template for in vitro transcription. Using the linearized plasmid solution without purification did not adversely affect the efficiency of transcription. To increase transcription efficiency, it was necessary to optimize each component, but the reaction followed general protocol for in vitro transcription. The final concentrations of each component used for in vitro transcription were as follows: 80 mM HEPES-KOH (pH 7.5), 24 mM $MgCl_2$, 2 mM spermidine, 40 mM DTT, 1 U/µl RNase inhibitor, 3 mM rNTPs, 3.75 U/µl T7 RNA polymerase, 0.005% (w/v) BSA, and 35% (v/v) of the Fok I-digested plasmid solution. The plasmid used in this example was constructed to harbor T7 promoter sequence, so that T7 RNA polymerase was added for in vitro transcription. If the plasmid was constructed to fit another promoter, the corresponding RNA polymerase to the promoter is required. The linearized plasmid and spermidine, one of the components that can be added for in vitro transcription, are combined together at a low temperature to form a precipitate. To prevent that precipitation, other components were mixed first and the mixture was heated at 37° C. for 5 minutes. Then, the linearized plasmid solution was added lastly. The in vitro transcription was performed at 37° C. for 2 hours and the efficiency thereof was analyzed by electrophoresis using 2% agarose gel. As a result, the present inventors confirmed that HEPES buffer was more preferable than Tris buffer for the in vitro transcription herein and the amount of the solution containing the plasmid linearized by Fok I affected greatly on the yield of the final transcript. When the solution containing the plasmid linearized by Fok I was prepared by the same manner as described in example 2, it was preferred to add the linearized plasmid solution 35% by the total volume for in vitro transcription. Even when a higher volume was added, the yield of the final transcript was not increased. In example 1, two different plasmids were constructed; one was primary plasmid and the other was the one mutated from of the primary plasmid. When the mutated plasmid was used, the yield of the in vitro transcription was two times as high as the yield given by in vitro transcription using the primary plasmid, as expected. However, even when the non-mutated primary plasmid was used as a template for the in vitro transcription, the yield was enough. Therefore, any of the two plasmids could be used to realize the present invention.

Example 4

Preparation of Cellular Extract used for in vitro Translation

The microorganism used for the preparation of cellular extract in example 4 was *E. coli* BL21(DE3). The cellular extract containing protein synthesis machinery such as ribosome and initiation factor, essential elements for the production of a protein by in vitro translation, was prepared from the microorganism. More particularly, BL21(DE3) was cultured in 5 ml of LB medium (trypton, 10 g/L; yeast extract, 5 g/L; NaCl, 10 g/L) at 37° C. for 7-8 hours. Then, the cultured broth was transferred in 100 ml of fresh LB medium, followed by further culture for overnight. After the culture, 100 ml of the culture broth was inoculated in a culture vessel containing 2 L of 2×TY (bacto-trypton, 16 g/l; yeast extract, 10 g/l; NaCl, 5 g/l). The culture temperature was 37° C. and the culture broth was continuously stirred at 860 rpm for complete mixing of the medium components and for the supplement of oxygen. After the initiation of culture, when the cells were grown until $OD_{600}$ reached 0.6, isopropylthio-β-D-galactoside (IPTG) was added to the medium at the final concentration of 1 mM in order to induce the expression of T7 RNA polymerase. After inducing the expression of T7 RNA polymerase, the culture continued until $OD_{600}$ was 4-5. Centrifugation was performed at 4,500 rpm at 4° C. for 12 minutes to recover the cultured cells. The obtained cell precipitate was resuspended in washing buffer (10 mM tris acetate, 14 mM magnesium acetate, 60 mM potassium acetate, 10 mM 2-mercaptoethanol, pH 8.2), followed by centrifugation again to recover the cells. The above processes were repeated three times to wash the cells. After the final centrifugation, the cell precipitate was resuspended in 30 ml of suspension buffer (10 mM tris acetate, 14 mM magnesium acetate, 60 mM potassium acetate, mM 2-mercaptoethanol, pH 8.2). Centrifugation was performed again at 12,000× at 4° C. for 30 minutes to recover the cells. S30 buffer (10 mM tris acetate, 14 mM magnesium acetate, 60 mM potassium acetate, 10 mM 2-mercaptoethanol, pH 8.2) was added to the precipitated cells at the ratio of 1.27 ml/1 g cell, followed by resuspension. The cells in the suspension were disrupted under the pressure of 770 psi using French presser, and as a result intracellular components were freed out from the cells. The cell lysate was centrifuged at 30,000× g at 4° C. for 30 minutes to obtain supernatant. The obtained supernatant proceeded to centrifugation under the same condition to obtain clearer supernatant. From the final supernatant, the layer right under the lipid layer was recovered. Preincubation buffer (293 mM Tris acetate, 2 mM magnesium acetate, 10.5 mM ATP, 84 mM creatine phosphate, 44 mM 2-mercaptoethanol, 0.04 mM each amino acid, 7 unit/ml creatine kinase, pH 8.2) was added to the recovered supernatant at the ratio of 3 ml per 10 ml, followed by preincubation at 37° C. for 80 minutes to destroy mRNA in the cellular lysate. After the preincubation, the incubation mixture was dialyzed at 4° C. for 45 minutes against 500 ml of S30 buffer to eliminate unnecessary elements or low molecular weight materials that could inhibit the protein synthesis. Dialysis was performed four times. Upon completion of dialysis, dialysate was recovered, followed by centrifugation at 4,000×g at 4° C. for 10 minutes to obtain supernatant. Aliquot of the recovered supernatant was stored in freezer containers, and then stored in liquid nitrogen. This supernatant was used as the cellular extract for cell-free protein synthesis. The cellular extract is commercially available. The cellular extract prepared in this example can be also used as the source for the separation of aminoacyl-tRNA synthetases necessary for aminoacylation in example 5.

Example 5

Separation of Enzyme (Aminoacyl-tRNA Synthetases) used for Aminoacylation 3 ml of the cellular extract prepared in example 4 was ultracentrifuged at 150,000×g at 4° C. for 2 hours using ultracentrifuge (BECKMAN) with 50.4 Ti rotor. Upon completion of the ultracentrifugation, the supernatant was recovered and stored at −70° C. The supernatant was used as the enzyme solution containing aminoacyl-tRNA synthetase for aminoacylation. The aminoacyl-tRNA synthetase can be either prepared or purchased. Most of the commercialized aminoacyl-tRNA synthetases in the market are more excellent in purity than the enzyme solution prepared in this example. So, it might be more preferred to purchase one of those commercialized enzymes. However, there is no big difference in results between using the purchased one or the prepared one.

Example 6

Coupling of Amino Acid with tRNA

The in vitro transcription mixture was added to be 40% of total reaction volume and the solution containing enough amount of the aminoacyl-tRNA synthetase prepared in example 5 was also added as shown in below. The aminoacylation mixture was incubated at 37° C. for 45 minutes to induce coupling of amino acid with tRNA. The in vitro transcription mixture was directly used for aminoacylation without purification, which did not adversely affect the efficiency of aminoacylation. The reaction mixture for aminoacylation (methionylation) contained 20 mM imidazole-HCl buffer (pH 7.5), 150 mM NaCl, 12.5 mM $MgCl_2$, 2 mM ATP, 68 μM folinic acid, 4 mM methionine, 40% (v/v) of the in vitro transcription mixture and 15% (V/V) of the solution containing the aminoacyl-tRNA synthetase prepared in example 5. These concentrations were determined through optimization. Folinic acid was not always necessarily added thereto. For the control, "total tRNA mixture" (15 nmol, $OD_{260}$=10) was used as a tRNA material instead of the in vitro transcription mixture. The methionylation was performed under the same conditions with the same compositions. After 45 minute methionylation, the reaction mixture was neutralized by adding one-tenth volume of 3 M sodium acetate (pH 5.0) to terminate methionylation. After termination of the methionylation, methionylated tRNA was extracted with an equal volume of acid phenol:chloroform (1:1, V/V; pH 5.0) as an aqueous phase. The aqueous phase was carefully recovered. Two and a half volumes of cold absolute ethanol were added to aqueous phase. The mixture was well mixed, which stood at −70° C. for 1 hour to precipitate the methionylated tRNA. One hour later, methionylated tRNA was isolated by centrifugation at 4° C. at 14,000 rpm for 20 minutes. The obtained precipitate of methionylated tRNA was resuspended in 40 μl of 62.5 mM sodium bicarbonate buffer (pH 8.5), which was later used for the conjugation with fluorophore in example 7 and for the conjugation with biotin in example 8 as the aminoacylated tRNA (methionylated tRNA).

Example 7

Conjugation of Fluorophore to Aminoacylated tRNA

To conjugate fluorophore to the aminoacylated tRNA (methionylated tRNA) prepared in example 6 (indicated as "methionine-tRNA conjugate" herein), the method of Gite, et al (Anal. Biochem. 279: 218-225, 2000) was used with slight modification. Fluorophore conjugation was performed using alpha-amino group of initiator methionine constituting the "methionine-tRNA conjugate". The fluorophore used in this example was exemplified by succinimidyl ester of 5-carboxyfluorescein (5-FAM) (Formula 1), succinimidyl ester of fluorescein-5-EX (Formula 2) having a spacer group added to increase flexibility in ester structures between fluorescein and succinimidyl ester, and succinimidyl ester of 6-((4,4-difluoro-5,7-dimethyl-4-bora-3a,4a-diaza-s-indacene-3-propionyl)amino) hexanoic acid (BODIPY) (Formula 3). BODIPY is a fluorescent material widely used for fluorescent labeling of cell-free synthesized protein.

[Formula 1]

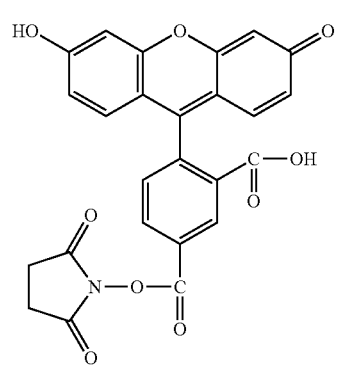

[Formula 2]

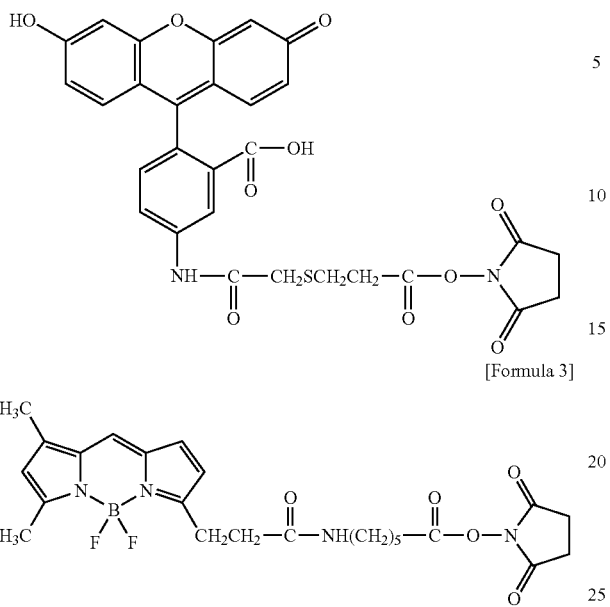

[Formula 3]

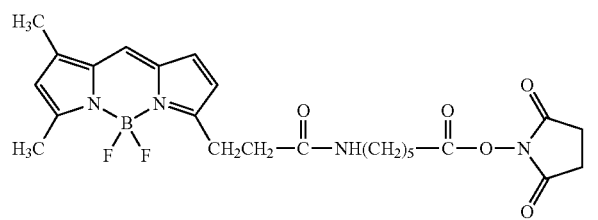

Particularly, a 10 μl of 30 mM succinimidyl ester of fluorescent dye in dimethyl sulfoxide (DMSO) was added to 40 μl of the "methionine-tRNA conjugate" solution prepared in example 6. The mixture was incubated in ice at 0° C. for 30 minutes to induce conjugation of fluorophore to the "methionine-tRNA conjugate". After incubation, the reaction was stopped by adding one-tenth volume of 2 M sodium acetate (pH 5.0). Upon termination of the reaction, fluorophore-conjugated "methionine-tRNA conjugate" was extracted repeatedly with an equal volume of acid phenol: chloroform (1:1, v/v; pH 5.0). Then, two and a half volumes of cold ethanol were added to the extracted aqueous phase and the mixture was allowed to stand at −70° C. for one hour to precipitate fluorophore-conjugated "methionine-tRNA conjugate". One hour later, the precipitated pellet was collected by centrifugation at 14,000 rpm at 4° C. for 20 minutes. The precipitate was dissolved in 50 μl of diethyl pyrocarbonate (DEPC)-treated RNAse-free water. Then, one-tenth volume of 2 M sodium acetate (pH 5.0) was added thereto. Two and a half volumes of cold ethanol were added thereto again, followed by ethanol precipitation once again. At last, centrifugation was performed at 14,000 rpm at 4° C. for 20 minutes to obtain a precipitate. This precipitate was washed once with 80% (v/v) ethanol solution. After washing, the precipitate was dried completely. Then, the dried precipitate was dissolved in 5 μl of DEPC-treated RNAse-free water. This solution was used later for the labeling of proteins produced by in vitro translation. The prepared fluorophore-conjugated "methionine-tRNA conjugate" (that is "tRNA conjugate for labeling") was analyzed by electrophoresis using 2% agarose gel. As a result, it was confirmed that the fluorophore-conjugated "methionine-tRNA conjugate" was successfully prepared as expected even though the tRNA was artificially synthesized by in vitro transcription.

Example 8

Conjugation of Biotin to Aminoacylated tRNA

The biotin-conjugated "methionine-tRNA conjugate" was prepared in this example by the same manner as described in example 7 except that biotin was used instead of fluorophore. The biotin derivative used herein was succinimidyl ester of biotin (Formula 4).

[Formula 4]

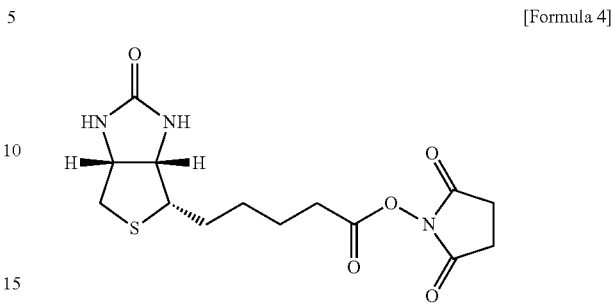

The prepared biotin-conjugated "methionine-tRNA conjugate" (that is "tRNA conjugate for labeling") was analyzed by electrophoresis using 2% agarose gel. As a result, it was confirmed that the biotin-conjugated "methionine-tRNA conjugate" was successfully prepared as expected even though the tRNA was artificially synthesized by in vitro transcription.

Example 9

Figure 3:
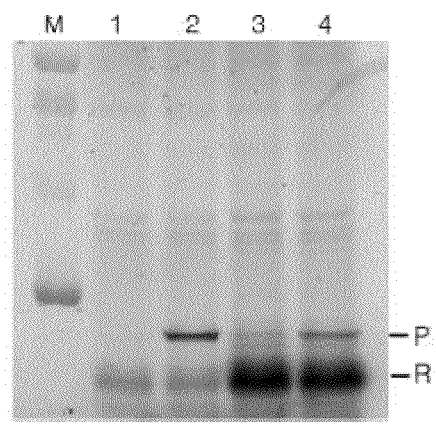
FIG. 3 is a photograph showing the comparison between cell-free synthesized proteins labeled with different "tRNA conjugates for labeling", one of which was prepared by using "total tRNA mixture" as a tRNA material and the other was prepared by using one type of tRNA generated by in vitro transcription as a tRNA material. CAT produced and labeled by one hour through in vitro translation was separated by SDS-PAGE and visualized by laser irradiation. Lane M shows a molecular weight marker, lane 1 shows the negative control reaction performed with the "tRNA conjugate for labeling" prepared by using the specific tRNA prepared by in vitro transcription in the absence of CAT gene, lane 2 shows the reaction performed with the "tRNA conjugate for labeling" prepared by using the specific tRNA prepared by in vitro transcription in the presence of CAT gene, lane 3 shows the negative control reaction performed with the "tRNA conjugate for labeling" prepared by using "total tRNA mixture" in the absence of CAT gene, and lane 4 shows the reaction with the "tRNA conjugate for labeling" prepared by using "total tRNA mixture" in the presence of CAT gene. In this figure, P indicates the cell-free synthesized and fluorescently labeled CAT; and R indicates background fluorescence.

Protein Labeling by Fluorophore-Conjugated "Methionine-tRNA Conjugate" and Detection thereof In vitro translation was performed according to the method of Kim, et al (Eur. J. Biochem. 239:881-886, 1996) with slight modification. The reaction mixture for in vitro translation was as follows: 57 mM Hepes-KOH (pH 8.2), 1.2 mM ATP, 0.85 mM each of GTP, UTP and CTP, 1.7 mM DTT, 150 mM potassium glutamate, 80 mM ammonium acetate, 16 mM magnesium acetate, 0.17 mg/ml E. coli total tRNA mixture, 64 μM folinic acid, 0.3 U/ml creatine kinase, 0.5 mM each of amino acids, 28 mM creatine phosphate, 0.6 mM cAMP, 6.7 μg/ml of circular plasmid containing genetic information of the target protein to be produced, and 33% (v/v) cellular extract. To label the cell-free synthesized proteins, 1 μl of the fluorophore-conjugated "methionine-tRNA conjugate" solution prepared in example 7 was added for each 15 μl cell-free protein synthesis reaction. The reaction mixture was well mixed, followed by incubation at 37° C. for 1 hour. Upon completion of in vitro translation, a 5 μl sample of the cell-free protein synthesis reaction mixture was taken and subjected to SDS-PAGE. After SDS-PAGE, the labeled protein was analyzed by using laser irradiation device. In this example, CAT was used as a major protein model. To confirm the effectiveness of the present invention in relation to proteins, not only CAT but also EPO and DHFR were selected as model proteins. In the example using CAT as a model protein, the growing polypeptide was labeled with the "tRNA conjugate for labeling" derived from "in vitro transcribed tRNA" or the "tRNA conjugate for labeling" derived from "total tRNA mixture". The protein was visualized by laser irradiation and the results are shown in FIG. 3. As shown in FIG. 3, even though the "tRNA conjugate for labeling" derived from "in vitro transcribed tRNA" was prepared from the tRNA artificially synthesized by in vitro transcription, it was able to selectively label the protein produced by in vitro translation. The protein labeled with the "tRNA conjugate for labeling" derived from "in vitro transcribed tRNA" gave less background fluorescence, indicating the improved signals, than the protein labeled with the "tRNA conjugate for labeling" derived from "total tRNA mixture". Particularly, the protein labeled with the conventional method using "tRNA conjugate for labeling" derived from "total tRNA mixture" showed significant background fluorescence around the position of 15-25 kDa protein. However, the protein labeled by the present invention showed comparatively less background fluorescence at the same position, suggesting that this invention could be very effective in the detection of a protein having the corresponding molecular weight to that point.

Figure 4:
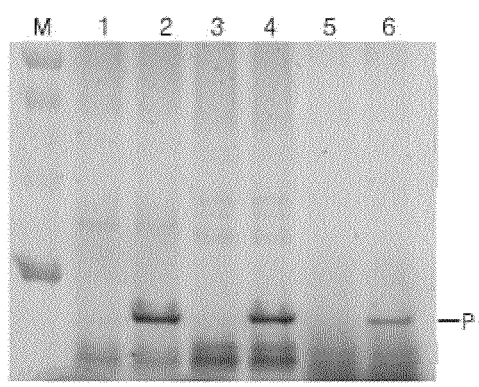
FIG. 4 is a photograph illustrating protein labeling and analysis using three different "tRNA conjugates for labeling" conjugated with different fluorophores. Lane M shows a molecular weight marker. Lane 1 shows the negative control reaction performed with the "tRNA conjugate for labeling" prepared by using 5-FAM succinimidyl ester as fluorophore in the absence of CAT gene. Lane 2 shows the reaction performed with the "tRNA conjugate for labeling" prepared by using 5-FAM succinimidyl ester as fluorophore in the presence of CAT gene. Lane 3 shows the negative control reaction performed with the "tRNA conjugate for labeling" prepared by using fluorescein-5-EX succinimidyl ester as fluorophore in the absence of CAT gene. Lane 4 shows the reaction performed with the "tRNA conjugate for labeling" prepared by using fluorescein-5-EX succinimidyl ester as fluorophore in the presence of CAT gene. Lane 5 shows the negative control reaction performed with the "tRNA conjugate for labeling" prepared by using BODIPY-FL succinimidyl ester as fluorophore in the absence of CAT gene. Lane 6 shows the reaction performed with the "tRNA conjugate for labeling" prepared by using BODIPY-FL succinimidyl ester as fluorophore in the presence of CAT gene. In this figure, P indicates the cell-free synthesized and fluorescently labeled CAT.

As shown in FIG. 4, CATs produced and labeled by one hour reaction performed by the said method using different fluorophore-conjugated "methionine-tRNA conjugate" were separated by SDS-PAGE, followed by visualization by laser irradiation. All the fluorophores used in this example were working appropriately. Therefore, it was confirmed that the conventional fluorophores being used for general protein labeling were all possible candidates for the present invention.

Figure 5:
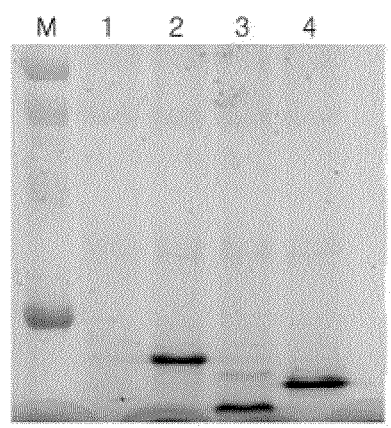
FIG. 5 is a photograph illustrating the result of experiment in which the present invention is applied to two other proteins except CAT. Lane M shows a molecular weight marker. Lane 1 shows the negative control reaction performed without the plasmid containing the genetic information. Lane 2 shows cell-free synthesized and fluorescently labeled CAT protein. Lane 3 shows cell-free synthesized and fluorescently labeled EPO protein. Lane 4 shows cell-free synthesized and fluorescently labeled DHFR protein.

It was also investigated whether or not the present invention is applicable and effective in other protein models. Precisely, CAT, EPO, and DHFR were labeled according to the method of the present invention. FIG. 5 is a photograph illustrating the visualization of different proteins realized by laser irradiation which were produced and labeled by the said one hour reaction and then separated by SDS-PAGE. As shown in FIG. 5, signals varied from proteins, but every protein was visualized as fluorescent band at the right position corresponding to its molecular weight. This result indicates that the present invention can be applied to every protein produced by in vitro translation. In this example, succinimidyl ester of 5-FAM was used as a fluorophore.

Example 10

Protein Labeling by Biotin-Conjugated "Methionine-tRNA Conjugate" and Detection thereof Labeling of the protein using the biotin-conjugated "methionine-tRNA conjugate" prepared in example 8 and detection of the same were performed as follows. Protein production by in vitro translation was performed by the same manner as described in example 9 only except that the biotin-conjugated "methionine-tRNA conjugate" solution was added to the cell-free protein synthesis reaction mixture instead of adding the fluorophore-conjugated "methionine-tRNA conjugate". Upon completion of in vitro translation, a 5 µl sample of the cell-free protein synthesis reaction mixture was taken and subjected to SDS-PAGE. After electrophoresis, western blotting was performed with the gel using avidin according to the standard protocol.

Figure 6:
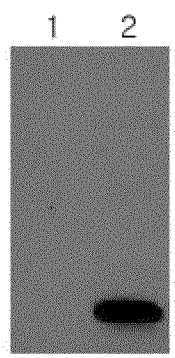
FIG. 6 is a photograph illustrating the result of the application of the present invention using the biotin-conjugated "tRNA conjugate for labeling", in which the cell-free synthesized and biotinylated EPO is visualized by western blotting after separation by SDS-PAGE. Lane 1 shows the negative control reaction performed with the biotin-conjugated "tRNA conjugate for labeling" prepared by using the specific tRNA produced by in vitro transcription in the absence of EPO gene.

Western blotting method with the biotin-labeled protein using avidin is well known to those in the art, so that detailed explanation is not given herein. EPO was used as a model protein in this example. FIG. 6 is a photograph illustrating the produced EPO labeled with biotin and visualized by western blotting after separation by SDS-PAGE. As shown in this Figure, even though the "tRNA conjugate for labeling" derived from "in vitro transcribed tRNA" was prepared from the tRNA artificially synthesized by in vitro transcription, it was able to label the protein produced by in vitro translation selectively.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A preparation method of a fluorophore or biotin conjugated aminoacylated tRNA derived from in vitro transcribed tRNA, which comprises the following steps:
   1) preparing one type of in vitro transcribed tRNA including the 3'-terminal CA sequence corresponding to a codon on DNA of an amino acid selected for target protein labeling by in vitro transcription using linearized plasmid prepared by the Fok I restriction enzyme treatment of a circular plasmid, wherein the circular plasmid is made by a method comprising:
      (a) annealing of a sense oligonucleotide of SEQ ID NO: 1 and an antisense oligonucleotide of SEQ ID NO: 2 to prepare a double-stranded DNA fragment,
      (b) digesting the double-stranded DNA fragment prepared in step (a) with EcoR I and Pst I, and
      (c) inserting the restriction enzyme-treated double-stranded DNA fragment prepared in step (b) into an EcoR I and Pst I-digested pUC19 vector;
   2) performing conjugation of the in vitro transcribed tRNA prepared in step 1) and the selected amino acid by aminoacylation; and
   3) preparing a fluorophore or biotin conjugated aminoacylated tRNA by conjugating fluorophore or biotin to a functional group existing on the side chain of the amino acid or α-amino group of initiator methionine constituting the aminoacylated tRNA prepared in step 2).

2. The preparation method according to claim 1, wherein the fluorophore or biotin conjugated aminoacylated tRNA is prepared by conjugating the fluorophore or biotin to the functional group existing on the side chain of the amino acid constituting the aminoacylated tRNA prepared in step 2).

3. A method for labeling a selected target protein produced by in vitro translation by adding the fluorophore or biotin conjugated aminoacylated tRNA prepared according to claim 1 into an in vitro translation mixture before in vitro translation starts.

* * * * *